United States Patent
Ortiz

(10) Patent No.: US 7,470,275 B2
(45) Date of Patent: Dec. 30, 2008

(54) ANASTOMOTIC RING APPLIER DEVICE PROVIDING FORWARD AND RETROGRADE VISUALIZATION

(75) Inventor: Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 447 days.

(21) Appl. No.: 11/121,346

(22) Filed: May 3, 2005

(65) Prior Publication Data
US 2006/0253139 A1 Nov. 9, 2006

(51) Int. Cl.
*A61B 17/10* (2006.01)
(52) U.S. Cl. .................. 606/139; 600/173; 606/153
(58) Field of Classification Search ......... 606/153–156, 606/139; 227/176.1, 19, 175.1, 179.1, 178.1, 227/181.1, 180.1; 600/104, 106, 129, 173–176
See application file for complete search history.

(56) References Cited

U.S. PATENT DOCUMENTS

| | | | |
|---|---|---|---|
| 5,395,030 A | | 3/1995 | Kuramoto et al. |
| 5,425,738 A | * | 6/1995 | Gustafson et al. ........... 606/153 |
| 5,855,312 A | | 1/1999 | Toledano |
| 6,171,321 B1 | | 1/2001 | Gifford et al. |
| 6,451,029 B1 | | 9/2002 | Yeatman |
| 6,485,496 B1 | | 11/2002 | Suyker et al. |
| 2002/0099267 A1 | * | 7/2002 | Wendlandt et al. .......... 600/173 |
| 2003/0032967 A1 | | 2/2003 | Park et al. |
| 2005/0070921 A1 | * | 3/2005 | Ortiz et al. .................. 606/139 |
| 2006/0206122 A1 | * | 9/2006 | Copa et al. .................. 606/153 |

FOREIGN PATENT DOCUMENTS

EP 1520531 6/2005

OTHER PUBLICATIONS

Office Action dated Jan. 4, 2006, for U.S. Appl. No. 10/675,497, filed Sep. 30, 2003.
European Search Report, dated Sep. 18, 2006, for EP Application No. 06252336.0.

* cited by examiner

*Primary Examiner*—Todd E Manahan
*Assistant Examiner*—Jennifer L Hornberger
(74) *Attorney, Agent, or Firm*—Frost Brown Todd LLC

(57) ABSTRACT

A surgical instrument for deploying an anastomotic ring device comprises a ring deployment mechanism, which is configured to receive and deploy an anastomotic ring. The instrument further comprises an imaging element that is operable to capture an image of the anastomosis site. In one version, the instrument is operable to capture both a forward view and a retrograde view of the anastomosis site.

20 Claims, 17 Drawing Sheets

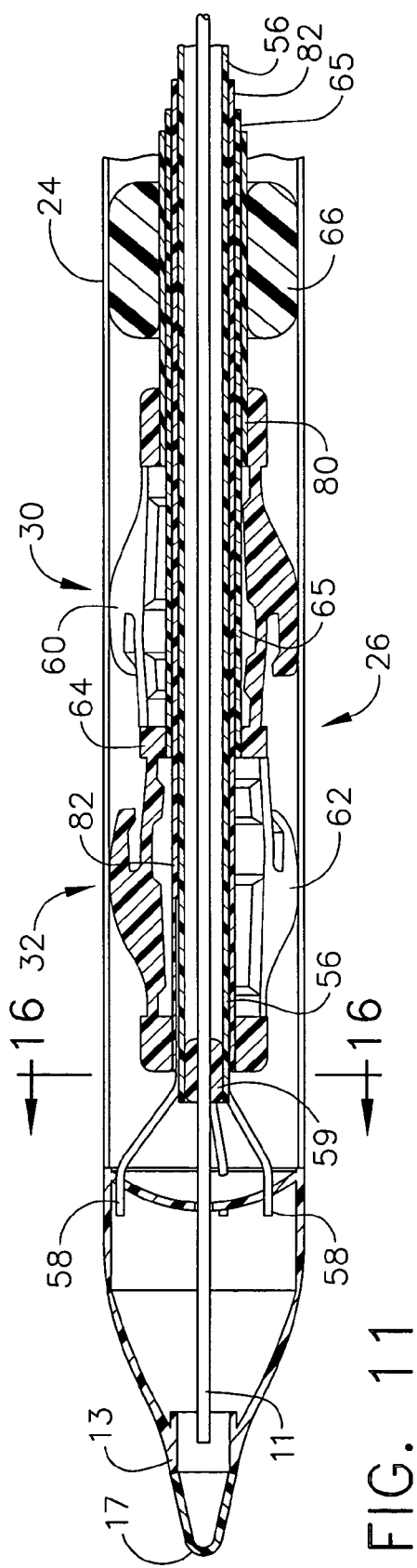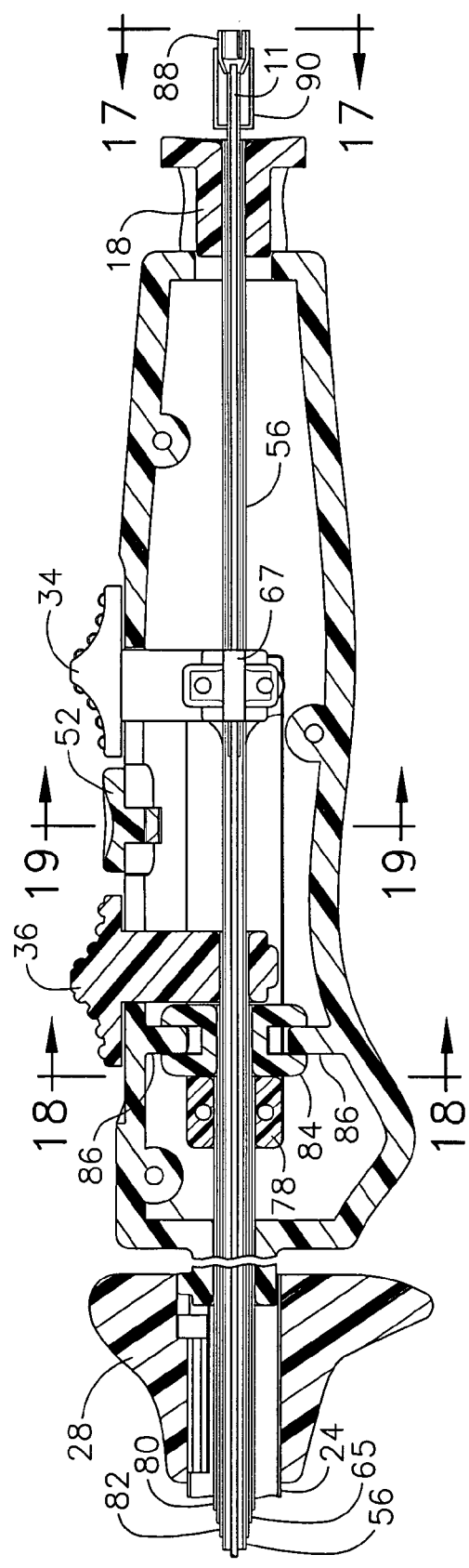
FIG. 11
FIG. 12

ANASTOMOTIC RING APPLIER DEVICE PROVIDING FORWARD AND RETROGRADE VISUALIZATION

FIELD OF THE INVENTION

The present invention relates, in general, to surgery and, more particularly, to a device for performing a surgical procedure on the digestive system.

BACKGROUND OF THE INVENTION

The percentage of the world population suffering from morbid obesity is steadily increasing. Severely obese persons may be susceptible to increased risk of heart disease, stroke, diabetes, pulmonary disease, and accidents. Because of the effects of morbid obesity on the life of the patient, methods of treating morbid obesity have been the subject of intense research.

One known method for treating morbid obesity includes the use of anastomotic rings. Devices for applying anastomotic rings are known in the art. Devices of this nature are commonly adapted to insert a compressed anastomotic ring to an anastomotic opening formed between proximate gastrointestinal tissue walls. These applier devices may utilize a ring deployment mechanism comprising an expansion element that is actuated once the compressed ring is placed in the anastomotic opening, causing the anastomotic ring to expand from its compressed, cylindrically-shaped position to an actuated, hollow rivet-shaped position.

During use of such applier devices, it may be desirable for the surgeon to accurately place the applier device in the anastomotic opening to deploy the ring. Further, it may be desirable that the surgeon ensure that the anastomotic ring has been properly deployed, as an improperly deployed ring may lead to complications or failure of the device. While it is possible to insert an endoscope to view the site of the anastomotic attachment, this may disadvantageously add extra steps and cost to the surgery.

Consequently, it may be desirable to have a device for inserting and deploying an anastomotic ring at the anastomotic opening that allows the surgeon to visually confirm that the applier is properly located and that the anastomotic ring has been properly placed. It may also be desirable to have a visualization method that may be implemented with existing anastomotic ring applier technology with relatively little added cost.

BRIEF SUMMARY OF THE INVENTION

Several embodiments of the present invention provide an anastomotic ring applier device that allows the surgeon to view the anastomotic attachment site and to confirm proper deployment of the anastomotic ring.

In one embodiment, a surgical instrument comprises a handle connected by an elongated shaft to a ring deployment mechanism. The instrument further comprises an imaging element adapted to capture an image of the anastomosis site. This may allow the surgeon to view the anastomosis site without introducing other instruments into the surgical site.

In another embodiment, a surgical instrument comprises a handle connected by an elongated shaft to a ring deployment mechanism. The instrument further comprises an imaging element adapted to capture an image of a forward view and an image of a retrograde view of the anastomosis site. This embodiment may allow the surgeon to view both sides of the anastomotic attachment before and after deployment of the anastomotic ring.

In another embodiment, an instrument comprises an actuating member configured to receive an anastomotic ring and move it from a compressed, cylindrical position to an actuated, hollow rivet-forming position in response to a compressive actuating force. The instrument also comprises a handle and an actuation mechanism for producing the actuating force, along with an elongated shaft connecting the handle to the actuating member. The instrument further includes an imaging element operable to capture an image of the anastomosis site. In this embodiment, the surgeon may view the anastomosis site before the anastomotic ring is deployed from an unactuated position, and may also view the anastomosis site after the ring has been moved to an actuated position to ensure that the ring has properly been deployed in a hollow rivet-forming position.

BRIEF DESCRIPTION OF THE FIGURES

The accompanying drawings, which are incorporated in and constitute a part of this specification, illustrate versions of the invention, and, together with the general description of the invention given above, and the detailed description of the versions given below, serve to explain the principles of the present invention.

FIG. 11 is cross-sectional view of a distal portion of the device of FIG. 1.

FIG. 12 is a cross-sectional view of a proximal portion of the device of FIG. 1.

DETAILED DESCRIPTION OF EMBODIMENTS OF THE INVENTION

Figure 1:
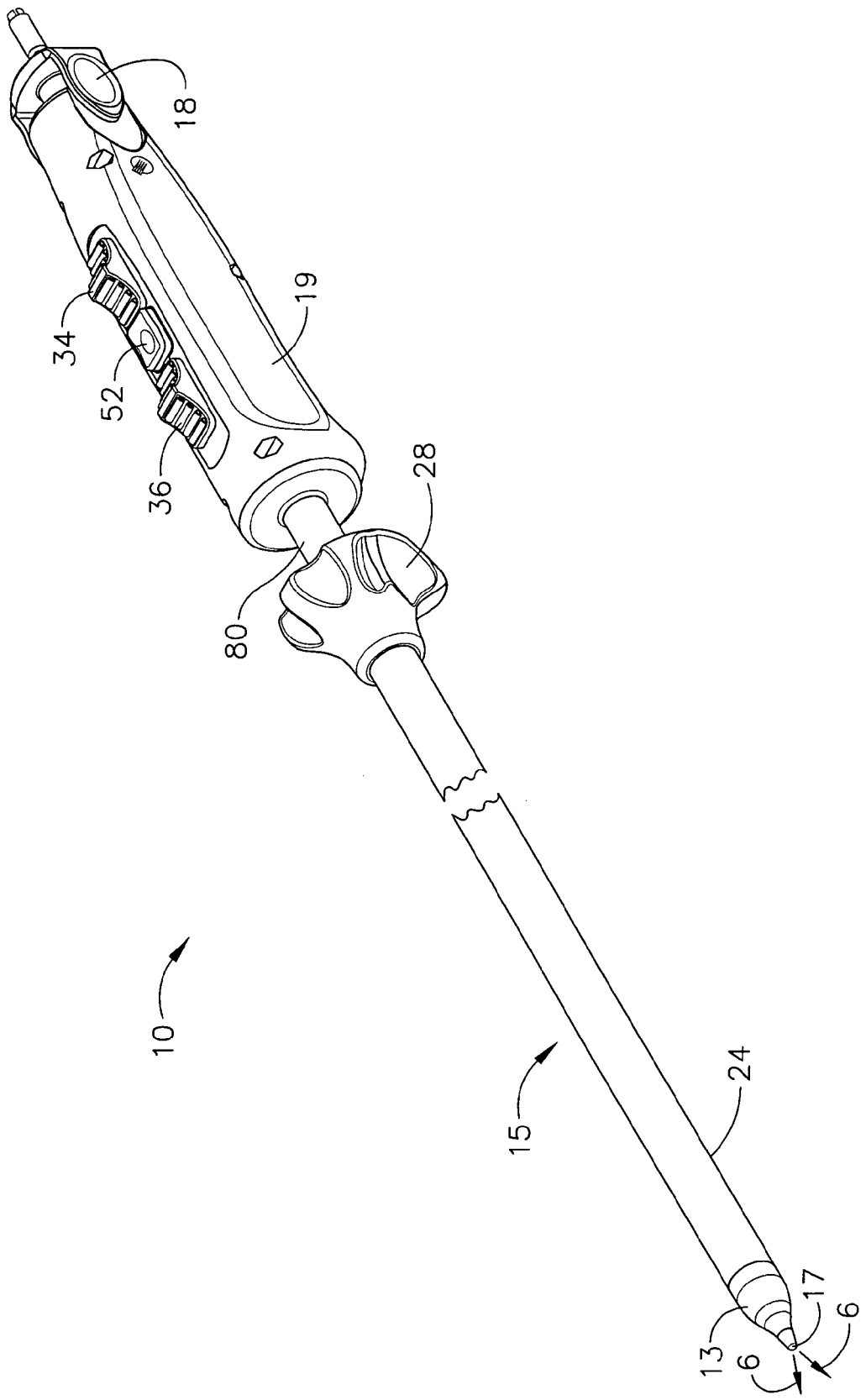
FIG. 1 is a perspective view of an anastomotic ring applier device, shown with a retracted tip.
Figure 2:
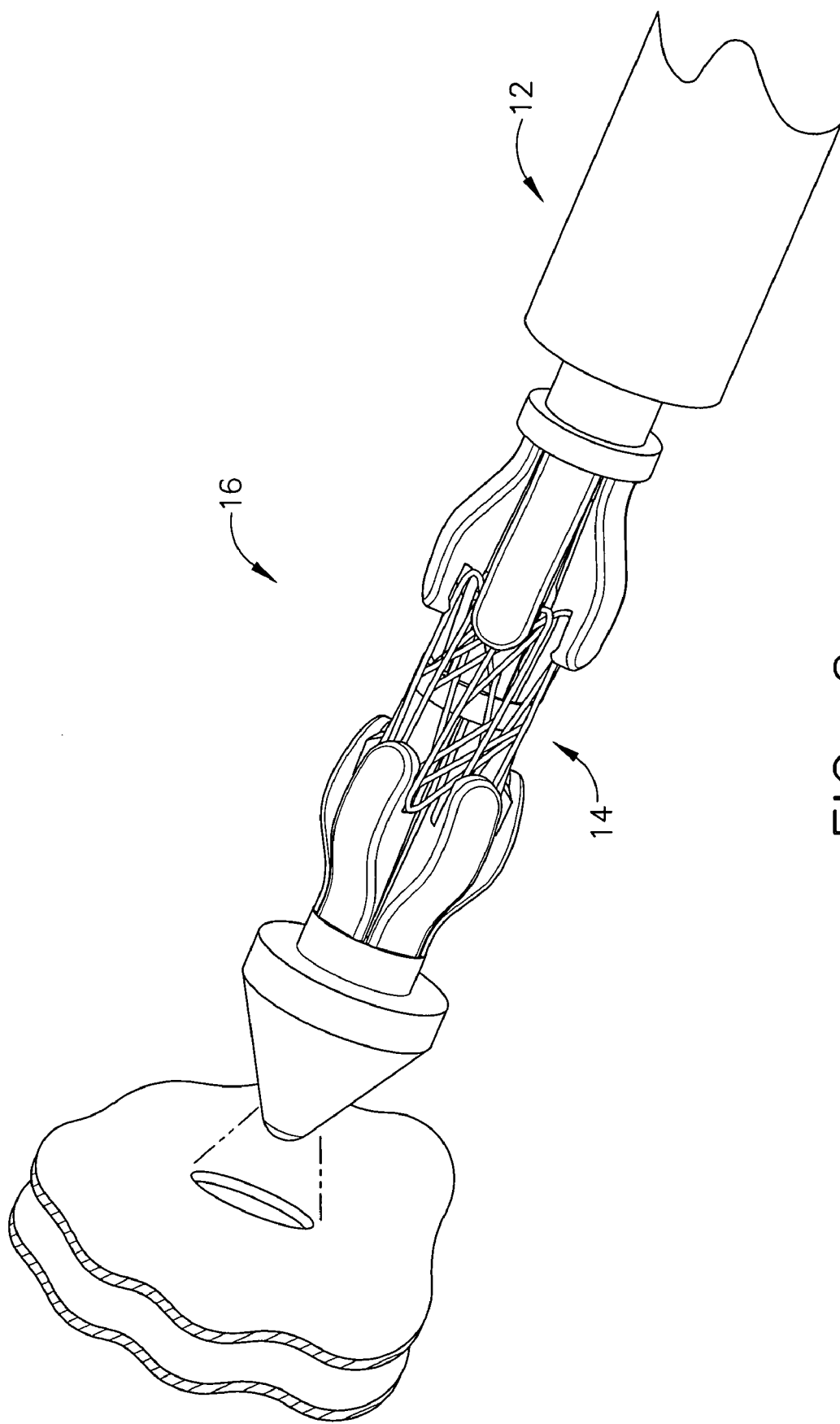
FIG. 2 is a partial perspective view of the distal portion of an anastomotic ring applier device holding an anastomotic ring in an unactuated position.
Figure 3:
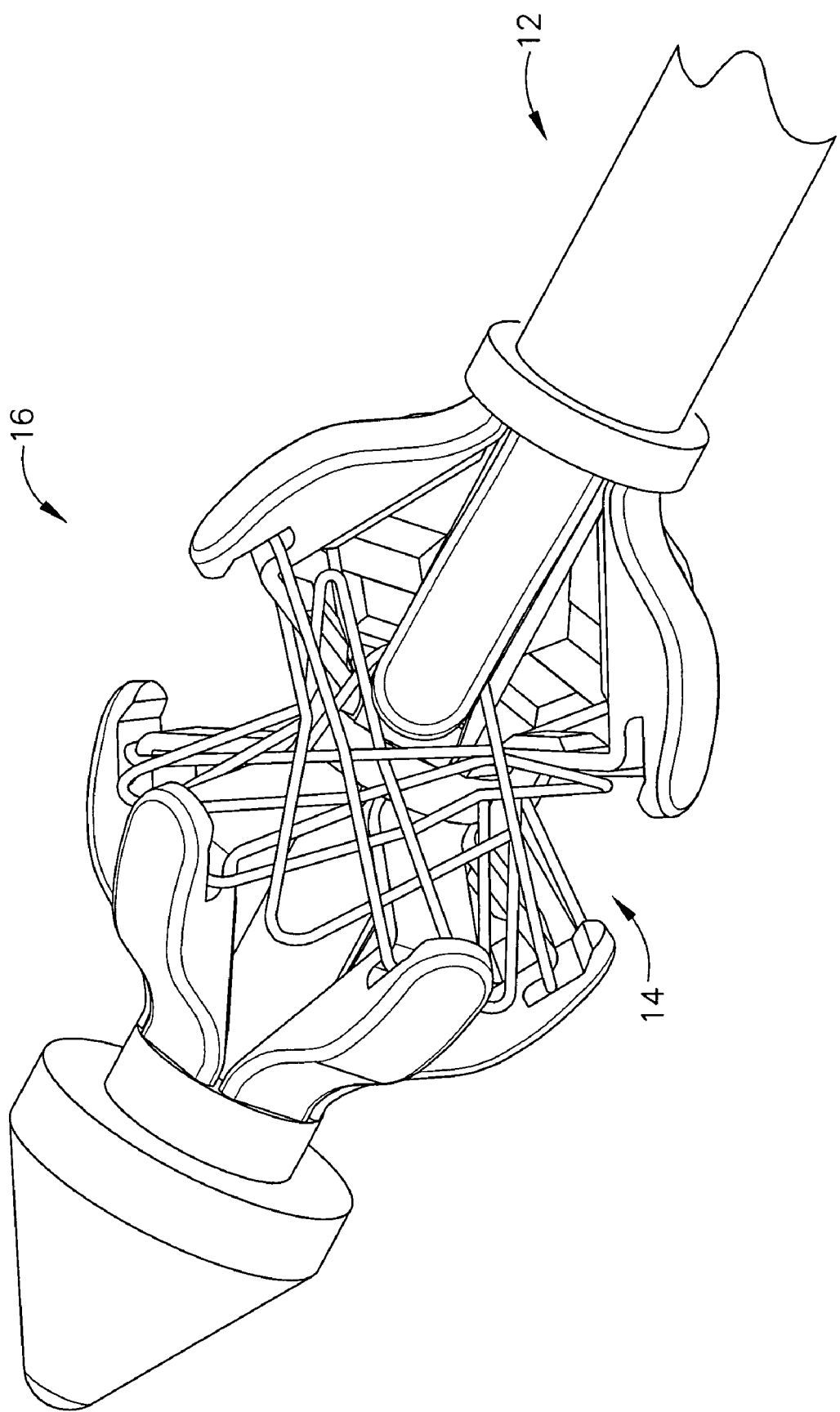
FIG. 3 is a partial perspective view of the distal portion of the device of FIG. 2 holding an anastomotic ring in the actuated position.
Figure 4:
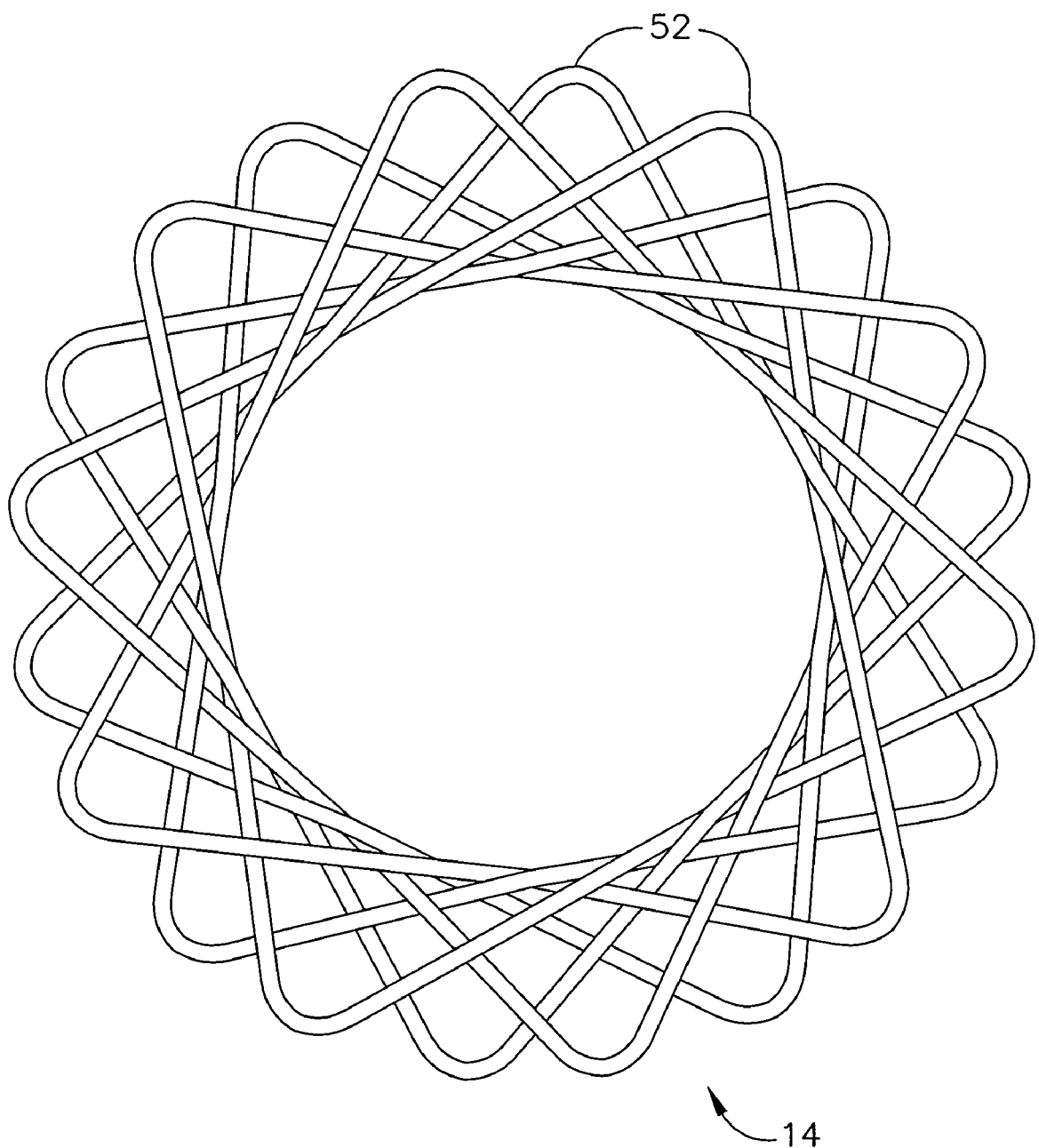
FIG. 4 is a frontal view of an actuated anastomotic ring.

Turning to the Drawings, wherein like numerals denote like components throughout the several views, FIG. 1 depicts an applier 10 that is operable to deploy and actuate an anastomotic ring device (not pictured in FIG. 1) from a generally cylindrical shape to one having properties of a hollow rivet, or ring, capable of forming an anastomotic attachment at an anastomosis target site, such as in a bariatric gastric bypass of a morbidly obese patient. FIG. 2 depicts another applier 12. It will be appreciated that appliers 10, 12 may be used in a variety of ways, including but not limited to laparoscopically or endoscopically. Applier 12 is shown in FIG. 2 with an anastomotic ring 14 on a deployment mechanism 16. In FIG. 2, anastomotic ring 14 is shown in the compressed, cylindrically-shaped position. In FIG. 3, deployment mechanism 16 of applier 12 has moved anastomotic ring 14 to the actuated, hollow rivet-shaped position. FIG. 4 is a close-up view of anastomotic ring 14 in the actuated position. Anastomotic ring 14 may comprise a shape memory effect (SME) material, such as nitinol by way of example only, that further assists in actuation to an engaging hollow rivet shape. Other suitable anastomotic ring 14 materials will be apparent to those of ordinary skill in the art. An exemplary anastomotic ring 14 is described in detail in U.S. Patent Application Publ. No. U.S. 2003/0032967 to Park et al.

It will be appreciated that the terms "proximal" and "distal" are used herein with reference to a clinician gripping a handle of applier 10. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure or other procedures. Use herein of one of these or similar terms should not be construed to limit the present invention for use in only one category of surgical procedure.

In the present example, applier 10 is configured to allow forward and retrograde visualization of an anastomotic site and a deployed anastomotic ring. Applier 10 comprises an imaging element 11 (FIG. 11). Imaging element 11 is configured to provide forward visualization and retrograde visualization. As shown in FIG. 1, imaging element 11 is configured to provide forward visualization through a tip 13 located at the distal end of an elongated shaft 15, as depicted by arrows 6. In order to allow imaging element 11 to capture a forward view, tip 13 comprises a clear tip point 17. Other suitable configurations for permitting imaging element 11 to capture a forward view will be apparent to those of ordinary skill in the art. In one embodiment, imaging element 11 comprises one or more imaging fibers.

Figure 5:
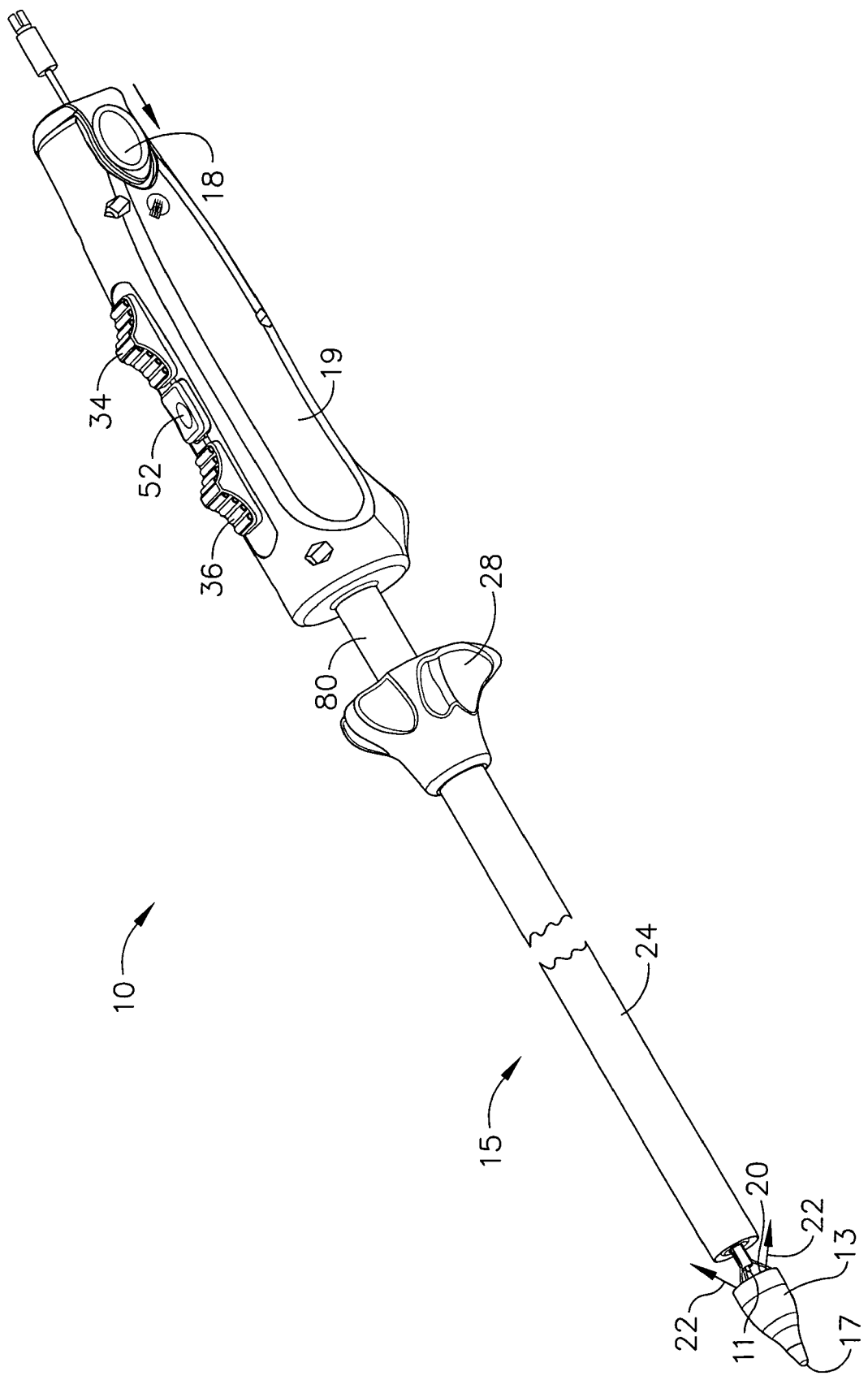
FIG. 5 is a perspective view of the device of FIG. 1, shown with the tip extended.
Figure 6:
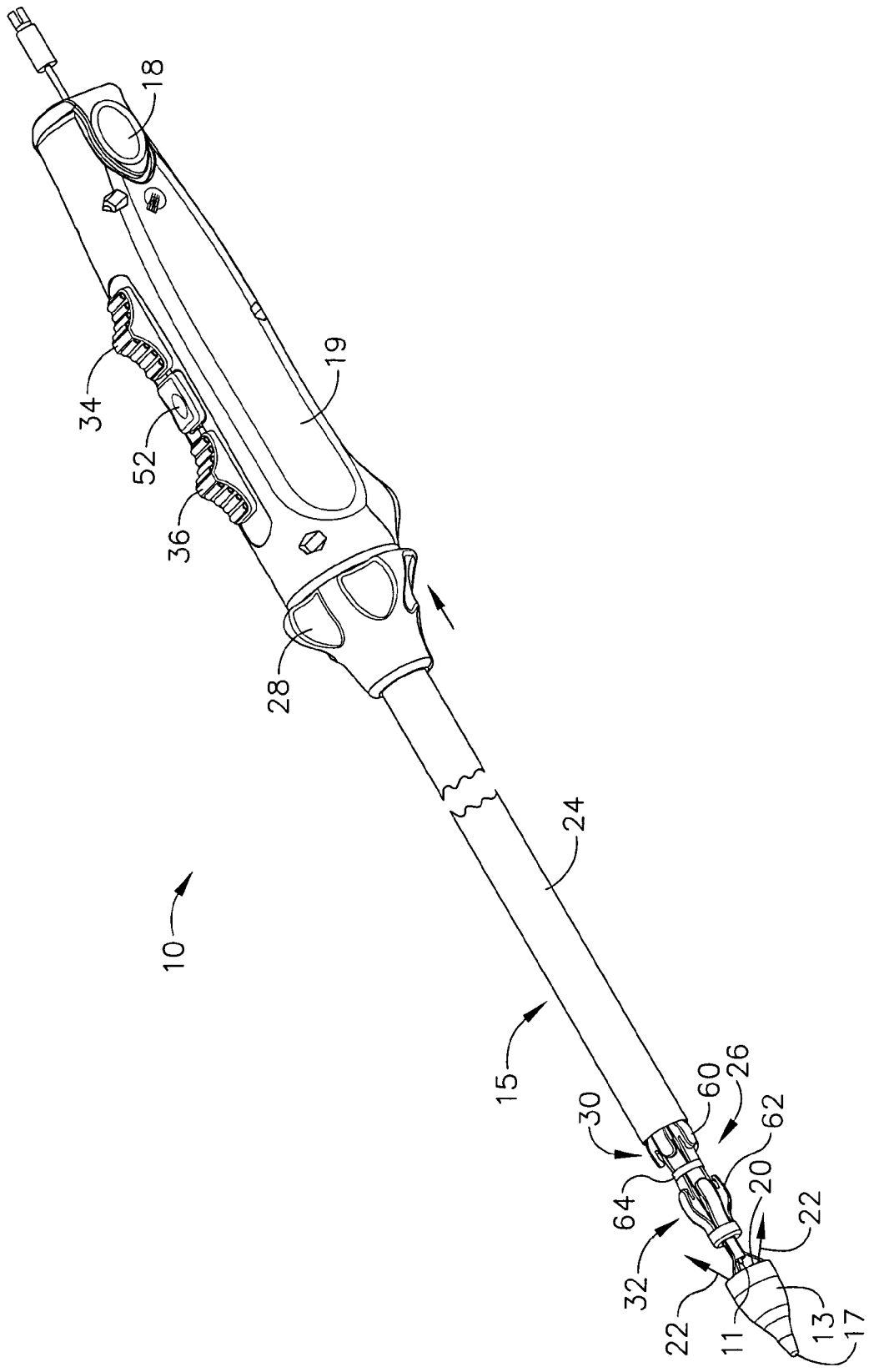
FIG. 6 is a perspective view of the device of FIG. 1, shown with the sheath retracted.

As shown in FIG. 5, applier 10 is also operable to provide retrograde visualization by moving tip 13 distally from a retracted position to an extended position. Applier 10 includes a tip actuator 18 located on a handle 19. Tip actuator 18 is operable to move tip 13 from a retracted position to an extended position. Tip 13 includes a proximal edge 20 comprising a mirrored surface. When tip 13 is in the extended position, imaging element 11 is configured to capture an image reflected off the mirrored proximal edge 20 of tip 13, thereby providing a retrograde view, as depicted by arrows 22. Alternatively, applier 10 may include one or more additional imaging elements positioned or operable to provide a retrograde view. Those of ordinary skill in the art will also appreciate that applier 10 may include one or more components other than a mirrored tip 13 to provide a retrograde view through imaging element 11, including but not limited to a mechanism operable to reposition or otherwise reconfigure imaging element 11. Still other methods and configurations for providing a retrograde view will be apparent to those of ordinary skill in the art.

In one embodiment, illumination is provided at the distal end of imaging element 11 by illumination fibers (not pictured) that run adjacent imaging element 11. It will be appreciated that such illumination may aid in the capture of images by imaging element 11 during use of applier 10. Suitable configurations of illumination fibers will be apparent to those of ordinary skill in the art. Of course, illumination may be provided by a variety of alternative means, devices, methods, and/or configurations.

Referring now to FIGS. 1 and 5-15, applier 10 of the present example has a shaft 15 comprising a tubular sheath 24. Tubular sheath 24 is moveable from a first position to a second position. In the first position, sheath 24 is configured to cover a ring deployment mechanism 26 (FIGS. 1 and 11) to prevent tissue from catching on deployment mechanism 26 during insertion and extraction of applier 10. Sheath 24 is configured such that deployment mechanism 26 is exposed and free to actuate when sheath 24 is in the second position. Applier 10 further comprises a sheath actuator 28 operable to move sheath 24 between the first and second positions. Suitable alternatives to sheath 24 and/or sheath actuator 28 will be apparent to those of ordinary skill in the art.

Figure 7:
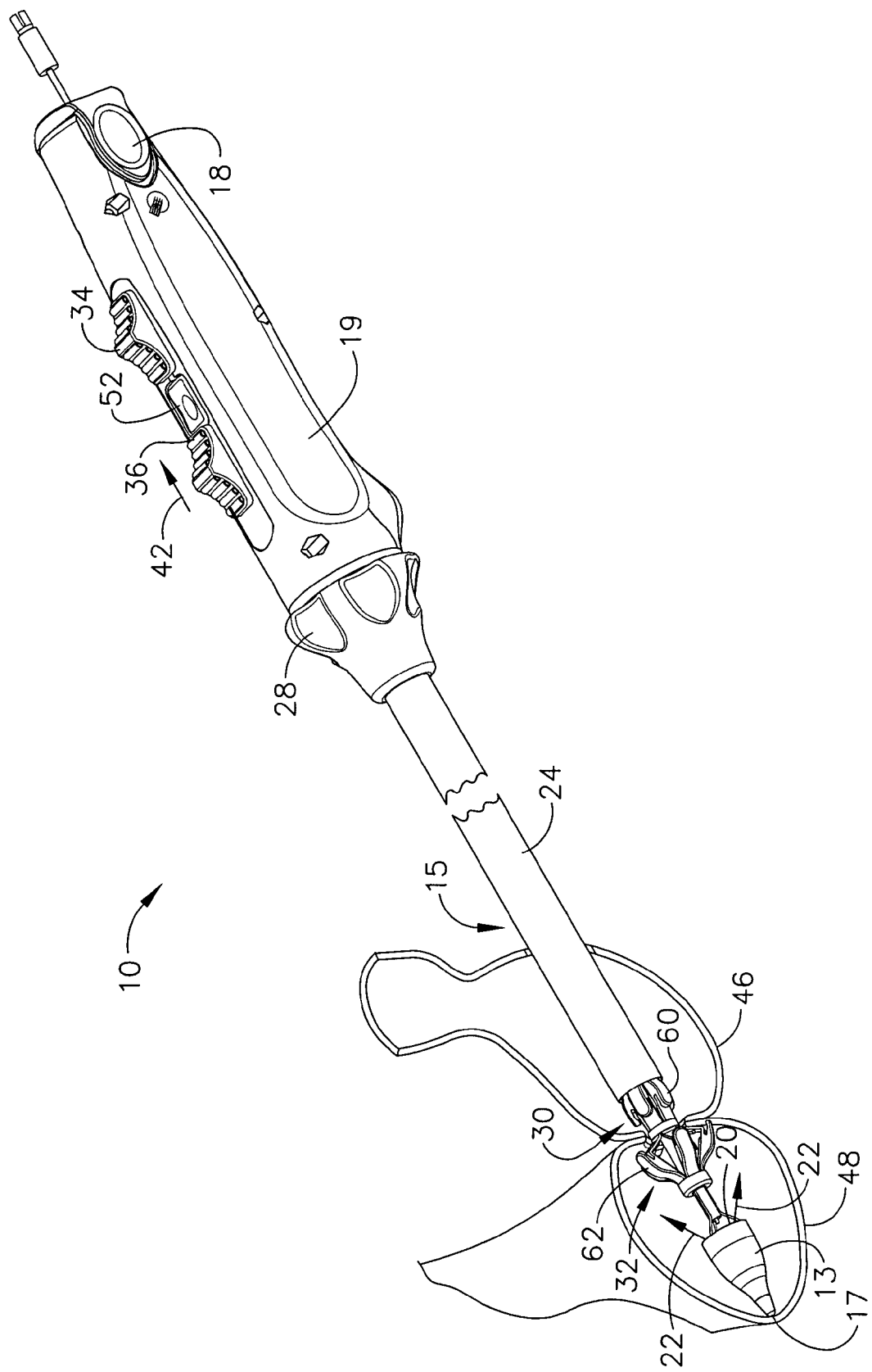
FIG. 7 is a perspective view of the device of FIG. 1, shown with a distal portion of the ring deployment mechanism actuated.
Figure 8:
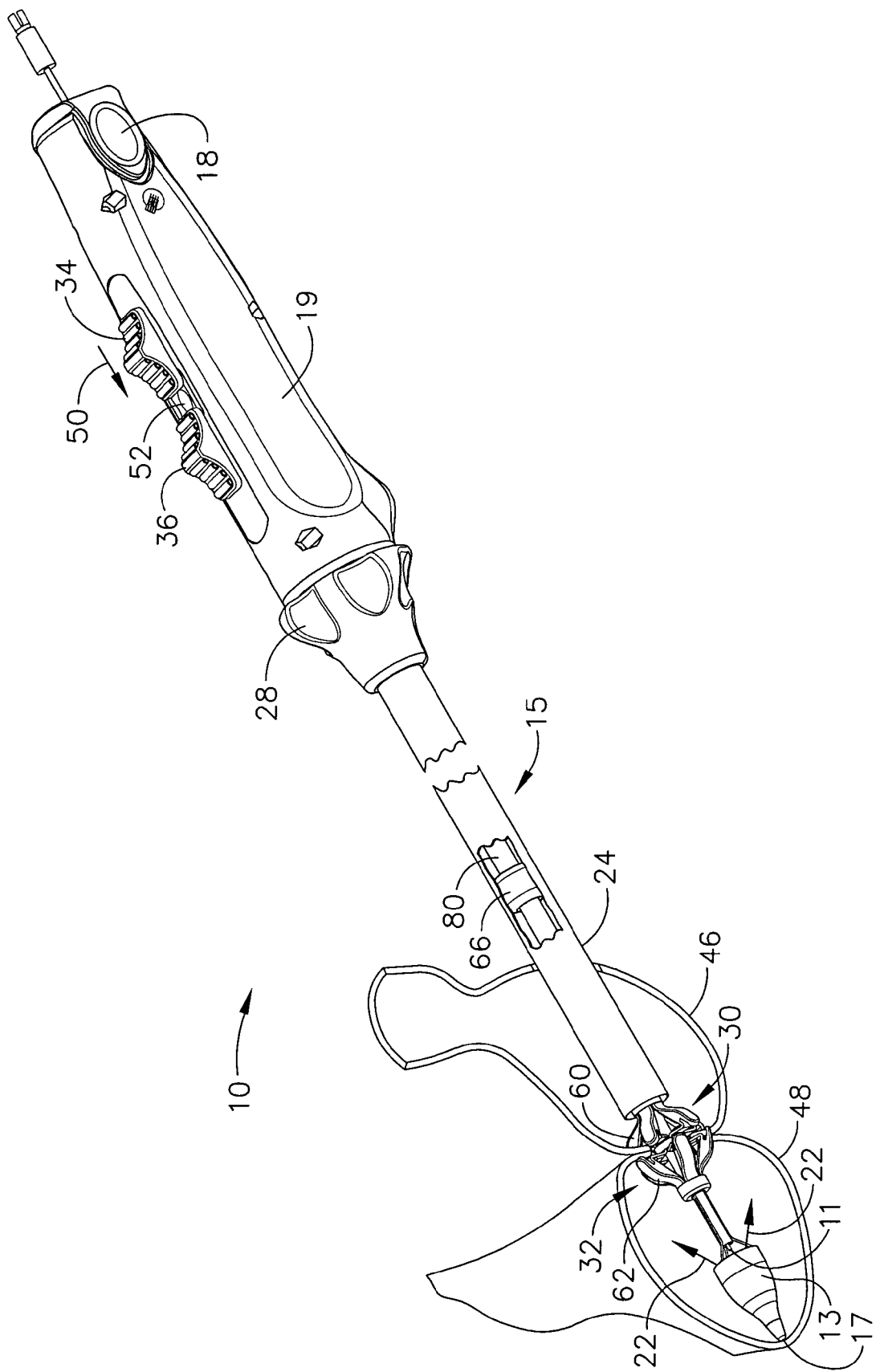
FIG. 8 is a perspective view of the device of FIG. 1, shown with both a distal portion and a proximal portion of the ring deployment mechanism actuated.
Figure 9:
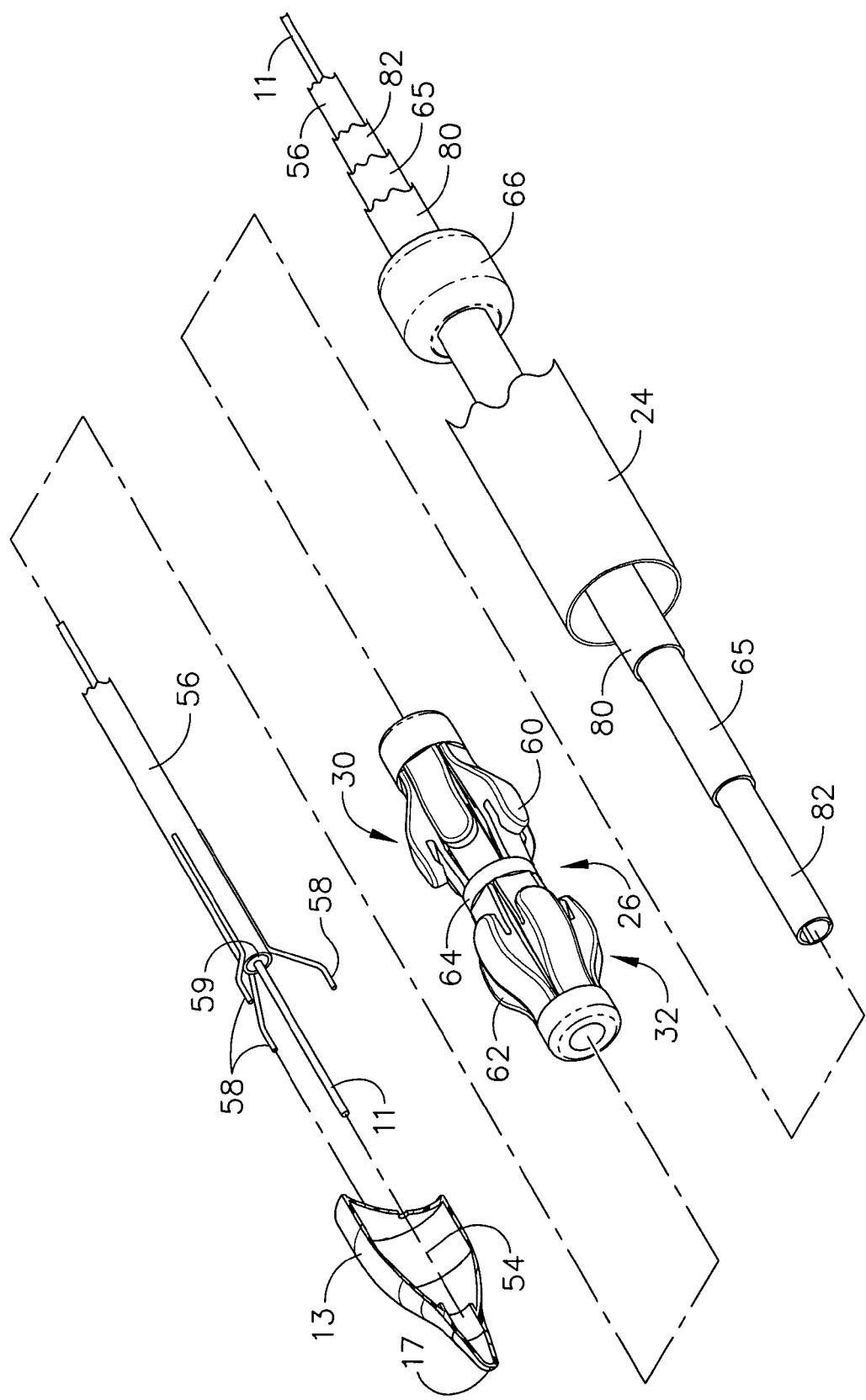
FIG. 9 is an exploded view of a ring deployment mechanism and a visualization system of the device of FIG. 1.
Figure 13:
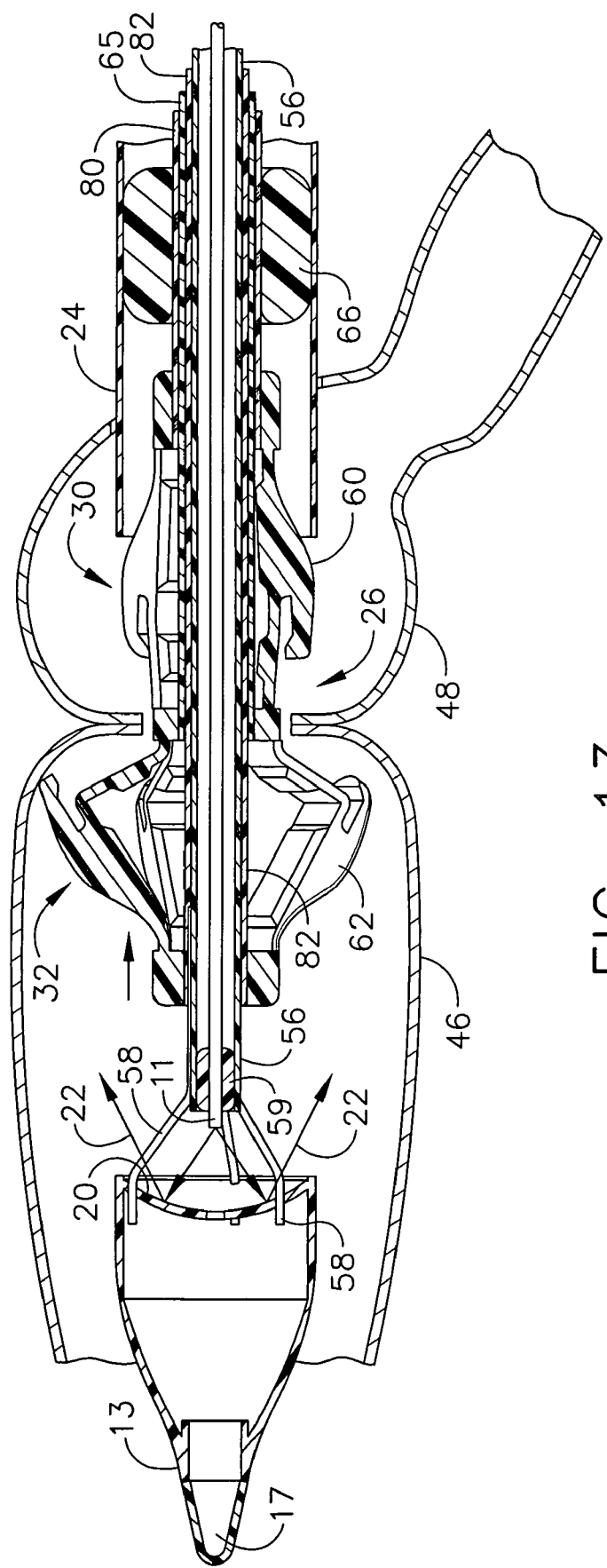
FIG. 13 is a cross-sectional view of a distal portion of the device of FIG. 1, shown inserted through an anastomotic opening with a distal portion of a ring deployment mechanism actuated.
Figure 14:
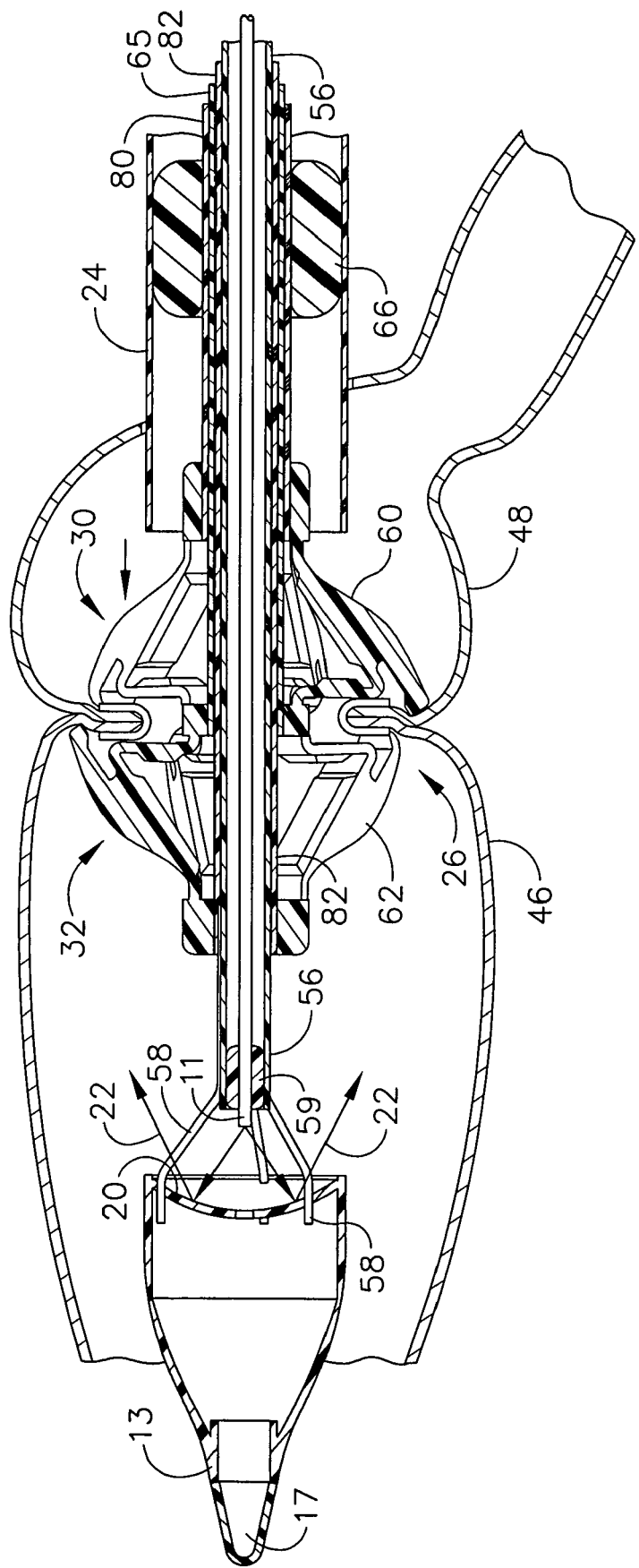
FIG. 14 is a cross-sectional view of a distal portion of the device of FIG. 1, shown inserted through an anastomotic opening with both a proximal and a distal portion of a ring deployment mechanism actuated.

Referring now to FIGS. 6-9 and 11-14, ring deployment mechanism 26 of the present example comprises a proximal portion 30 and a distal portion 32. Applier 10 further comprises a pair of deployment actuators 34, 36. As described in more detail below, first deployment actuator 34 is operable to actuate proximal portion 30 of ring deployment mechanism 26; and second deployment actuator 36 is operable to actuate distal portion 32. In FIGS. 7 and 13, distal portion 32 is shown in the actuated position for deploying a distal portion of an anastomotic ring 14. Arrow 42 depicts actuating motion of second actuator 36. In FIGS. 8 and 14, proximal portion 30 is shown in the actuated position for deploying a proximal portion of anastomotic ring 14 to complete an anastomotic attachment between proximate tissue walls 46, 48. Arrow 50 depicts the actuating motion of first actuator 34. Fingers 60, 62 are configured to hold an anastomotic ring 14 by engaging petals 51 prior to and during deployment of the anastomotic ring 14, and release petals 51 upon deployment of the anastomotic ring 14. It will be appreciated that any suitable alternative(s) to ring deployment mechanism 26 and/or deployment actuators 34, 36 may be used.

Figure 15:
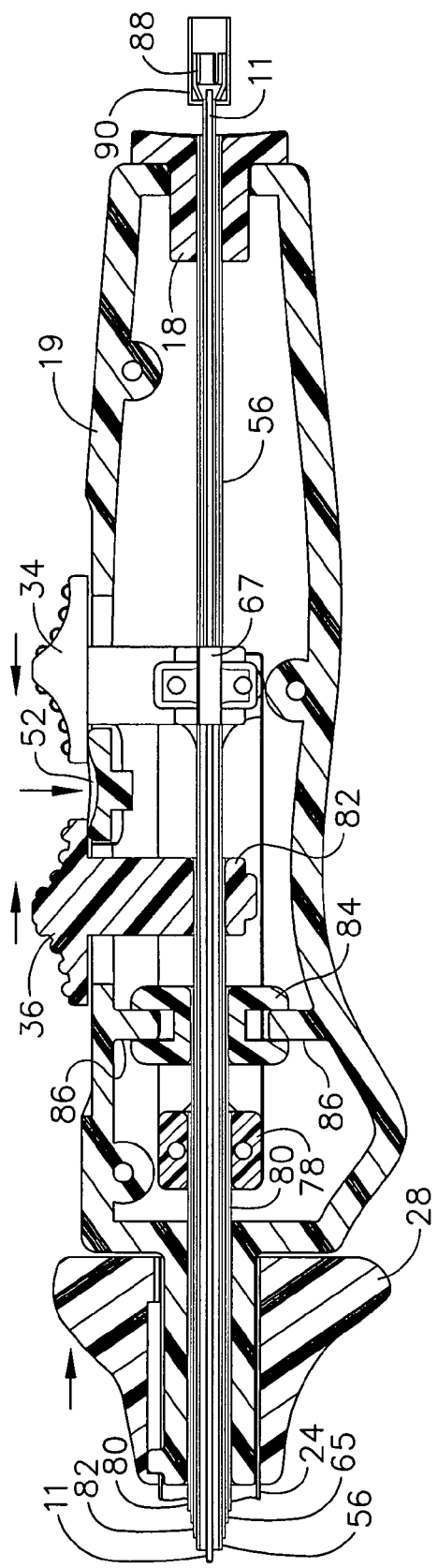
FIG. 15 is a cross-sectional view of a proximal portion of the device of FIG. 1, shown with ring deployment actuators in the actuated position, a sheath actuator in the retracted position and a locking element in the unlocked position.
Figure 16:
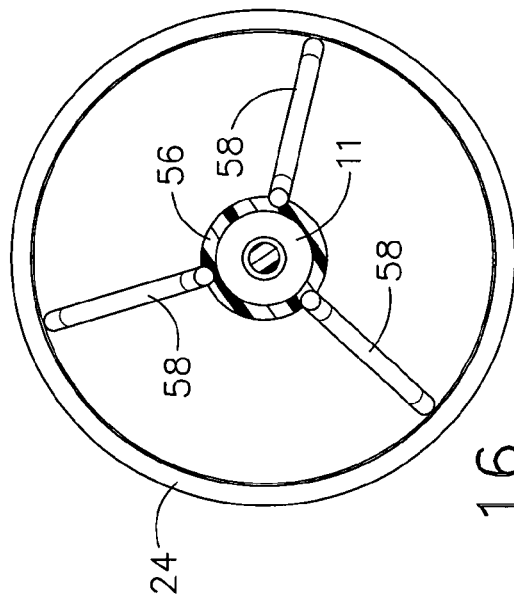
FIG. 16 is a cross-sectional view taken at Plane 16 of the device of FIG. 11.
Figure 17:
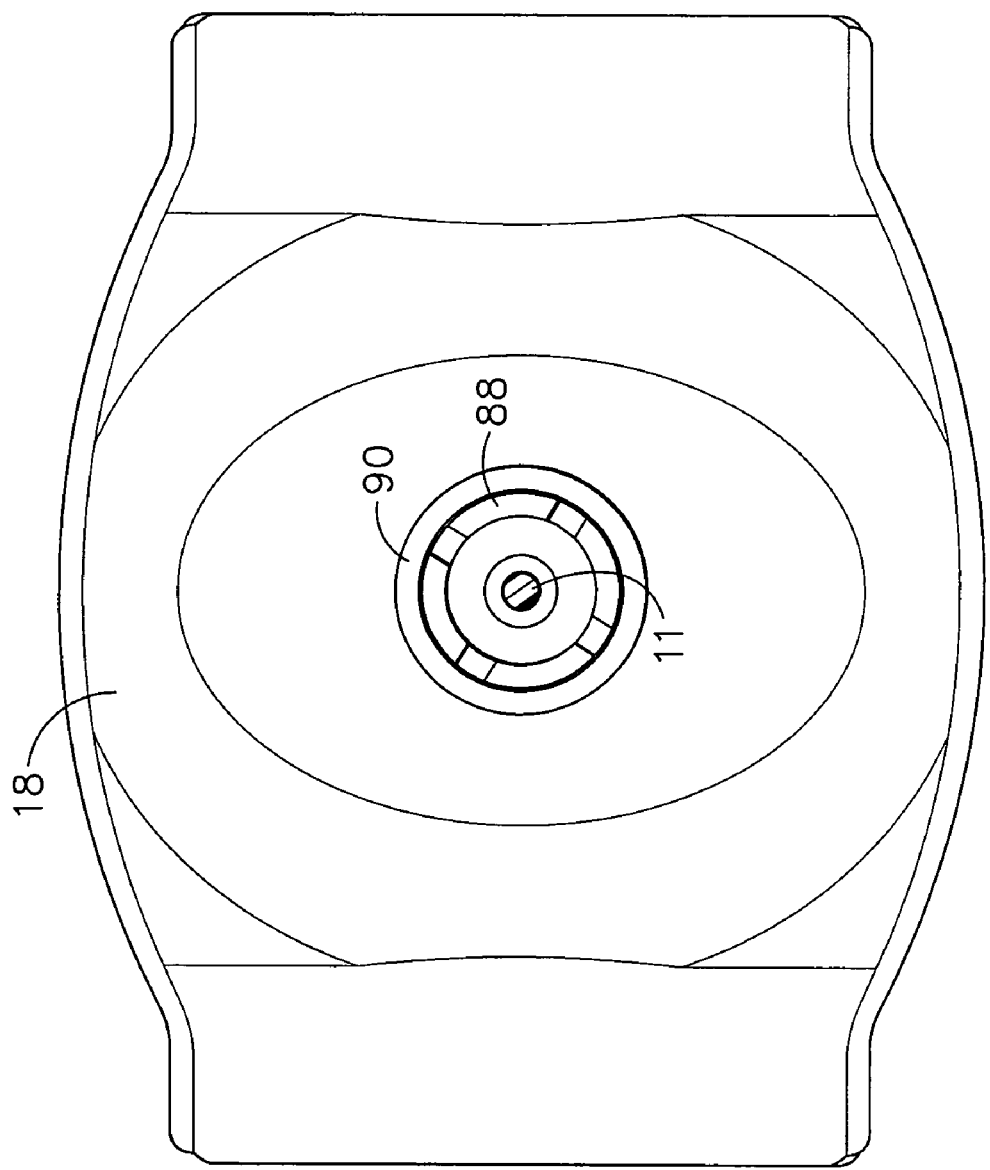
FIG. 17 is a cross-sectional view taken at Plane 17 of the device of FIG. 12.
Figure 18:
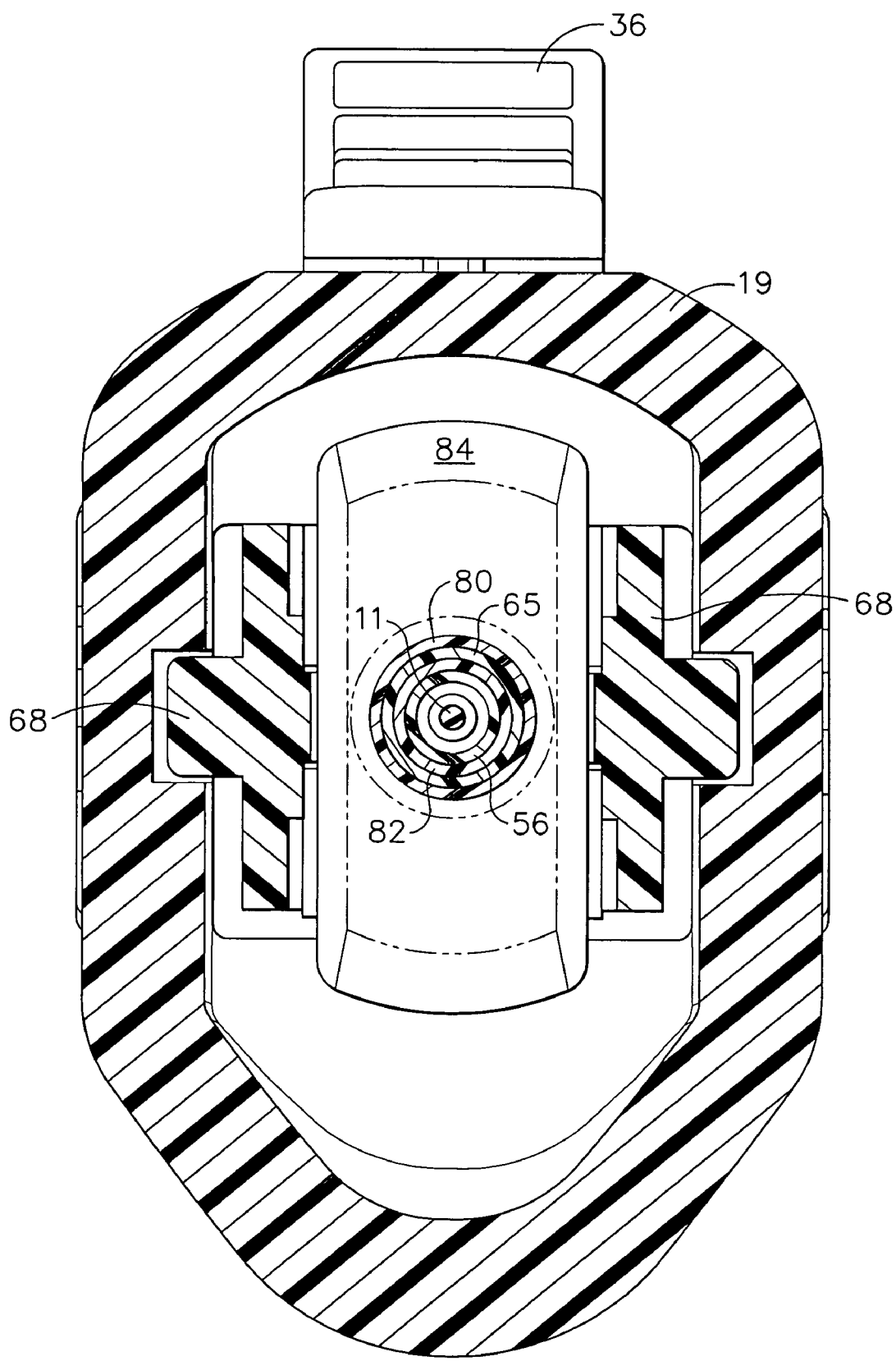
FIG. 18 is a cross-sectional view taken at Plane 18 of the device of FIG. 12.
Figure 19:
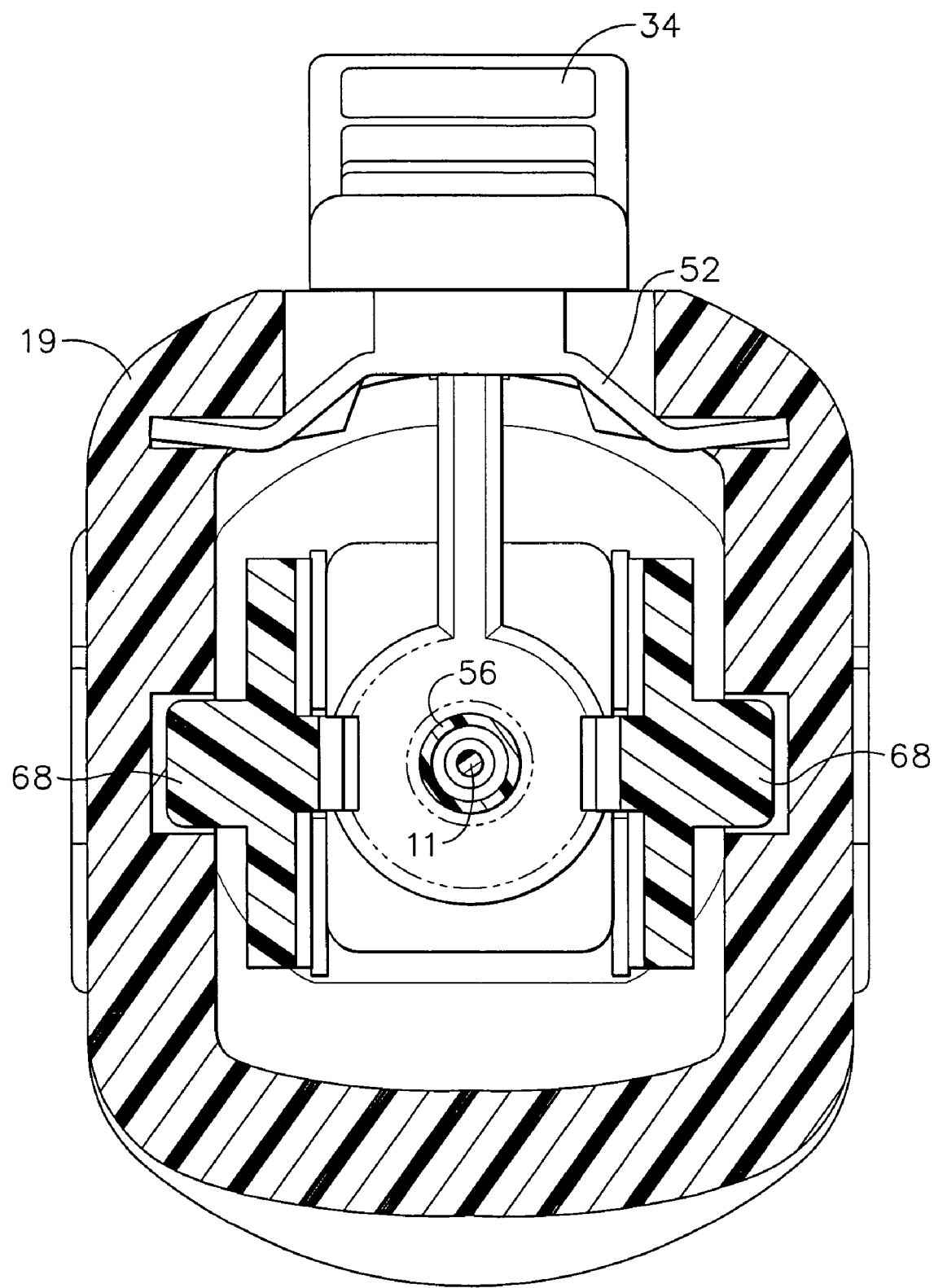
FIG. 19 is a cross-sectional view taken at Plane 19 of the device of FIG. 12.

To prevent inadvertent deployment of ring deployment mechanism 26, applier 10 of the present example is provided with a locking element 52. In the present example, locking element 52 is operable to move from a locked position to an unlocked position. In FIGS. 1, 5, 6, and 12, locking element 52 is shown in a locked position preventing actuating movement of first actuator 34 and second actuator 36. In FIGS. 7, 8, and 15, locking element 52 is shown in the unlocked position, allowing actuators 34, 36 to move to the actuated position.

Referring now to FIGS. 9, 11, 13, and 14, tip 13 is shown comprising a channel 54 allowing imaging element 11 to pass into tip 13 when tip 13 is in the retracted position. Imaging element 11 is passable through a guide tube 56. Guide tube 56 is slideable within shaft 15 and is in communication with tip actuator 18. The distal end of guide tube 56 comprises a plurality of connectors 58 that attach to tip 13. In this manner, tip actuator 18 is operable to communicate motion to tip 13 via guide tube 56 in order to move tip 13 between the retracted and extended positions. Guide tube 56 also comprises a bushing 59 that is configured to keep imaging element 11 centered. Suitable alternatives configurations of guide tube 56 will be apparent to those of ordinary skill in the art.

In the present example, proximal portion 30 of ring deployment mechanism 26 comprises a plurality of fingers 60; and distal portion 32 also comprises a plurality of fingers 62. Both proximal fingers 60 and distal fingers 62 are in a double-hinged relationship with a stationary mid-ring 64 of ring deployment mechanism 26. Proximal fingers 60 are configured to slide toward mid-ring 64 in response to engagement of first actuator 34, causing proximal fingers 60 to actuate outwardly from shaft 15. Mid-ring 64 is held stationary by a stationary ground tube 65. Likewise, distal fingers 62 are configured to slide toward mid-ring 64 in response to actuation of second actuator 36, causing distal fingers 62 to actuate outwardly from shaft 15. As shown in FIGS. 9, 11, 13, and 14, the above-described actuating components of ring deployment mechanism comprise a series of concentric tubes 82, 65, 80 within shaft 15. A bushing 66 (FIGS. 8, 9, 11, 13 and 14) is included within shaft 15 to keep the concentric tubes centered. It will be appreciated, however, that the above-described components need not be concentrically aligned, and that any suitable alternative to bushing 66 may be used.

As stated above, first deployment actuator 34 of the present example is operable to control proximal fingers 60 and second deployment actuator 36 is operable to control distal fingers 62. First and second ring deployment actuators 34, 36 each comprise a pair of grooves 67 that are adapted to slide on a track 68 (FIG. 10) of handle 19. The range of first actuator 34 is limited by the width of a slot 70, while the range of second actuator 36 is limited by the width of a slot 72. As mentioned above, locking element 52 may be utilized to prevent inadvertent movement of first or second actuators 34, 36 within slots 70, 72, respectively.

In the present example, first actuator 34 is fixedly attached to a proximal portion 74 of track 68. Track 68 is slideable within handle 19. A distal portion 76 of track 68 is fixedly attached to a slider 78, which is slideably engaged with handle 19. Slider 78 is fixedly connected to outer tube 80. Longitudinal motion of first actuator 34 is thereby operable to cause corresponding longitudinal motion of track 68, slider 78, and outer tube 80. Other suitable relationships between these components, as well as alternative components, will be apparent to those of ordinary skill in the art.

The proximal end of ground tube 65 is fixedly attached to anchor member 84. Anchor member 84 is configured to engage with bosses 86, which are integral with handle 19. Accordingly, in the present example, anchor member 84 and bosses 86 are configured to prevent relative movement between ground tube 65 and handle 19. Of course, any other configuration may be used.

Second actuator 36 is connected to an inner tube 82. Inner tube 82 extends longitudinally through ground tube 65. Inner tube 82 is operable to communicate motion to distal fingers 62. In this manner, first actuator 34 controls actuation of proximal fingers 60, and second actuator 36 controls actuation of distal fingers 62.

It should be noted that although second actuator 36 is configured to slide on track 68 in the present example, second actuator 36 is not statically attached to track 68. Therefore, longitudinal movement of track 68 caused by motion of first actuator 34 does not cause longitudinal movement of second actuator 36. Of course, handle 19 and components thereof may be configured in any other suitable way. By way of example only, first actuator 34 may be configured to control actuation of distal fingers 62, and second actuator 36 may be configured to control actuation of proximal fingers 60. Still other suitable alternative configurations will be apparent to those of ordinary skill in the art.

Figure 10:
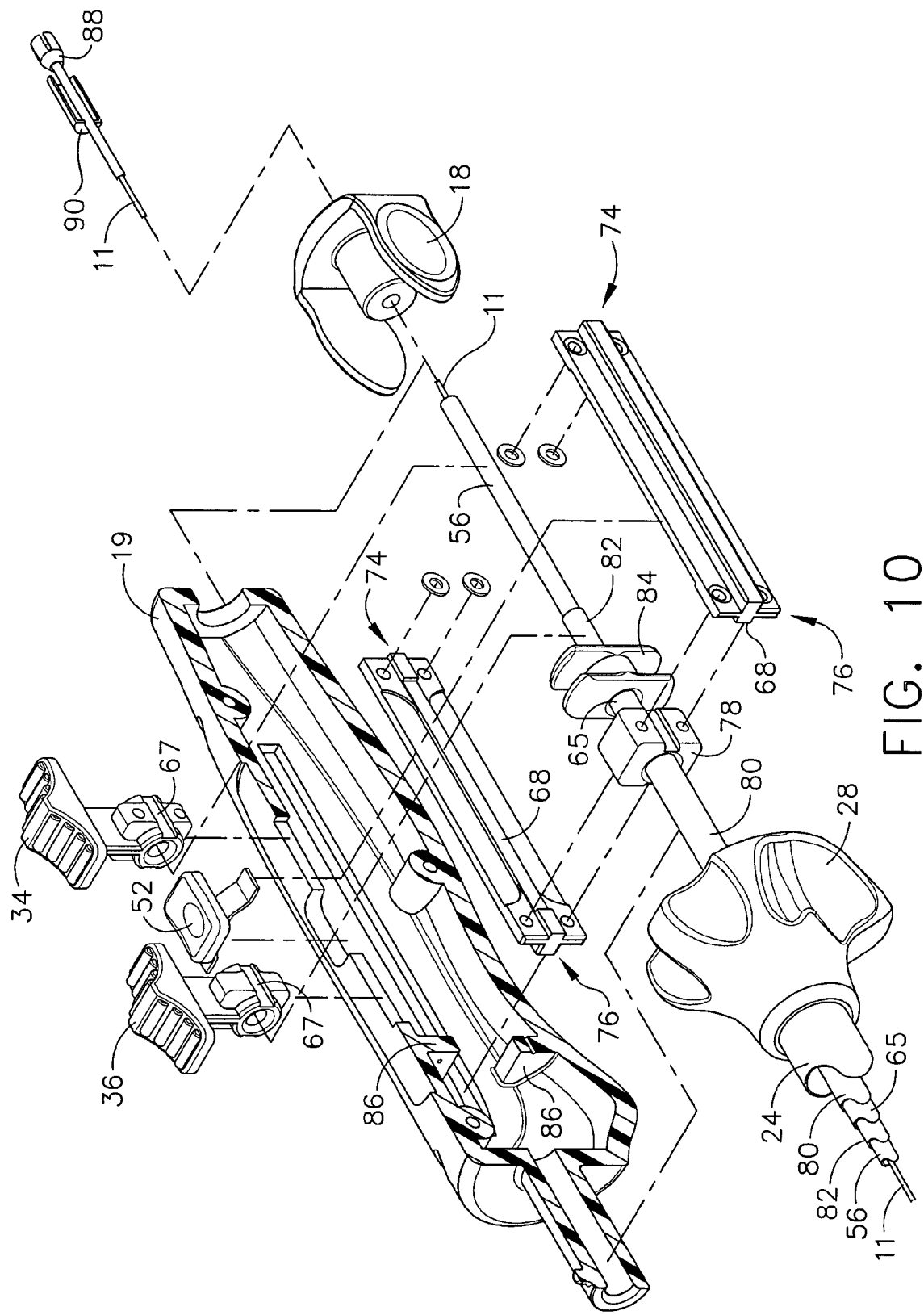
FIG. 10 is an exploded view of an actuation mechanism of the device of FIG. 1.

Referring to FIGS. 10, 12, and 15, the proximal end of imaging element 11 terminates into clamp 88, and is fixed thereto. Clamp 88 is configured to couple with an endoscope or other imaging device, which may be used to amplify or view the image captured by imaging element 11. A locking slide collar 90 is disposed about imaging element 11, and may be slid over clamp 88 to secure clamp 88 to an endoscope or other device. In the present example, imaging element 11 is not fixedly secured within applier 10. Thus, imaging element 11 may be pushed or pulled relative the applier 10 to longitudinally position imaging element 11. By way of example only, imaging element 11 itself or collar 90 may be grasped to accomplish such movement. Other suitable ways for positioning imaging element 11 will be apparent to those of ordinary skilled in the art. It will also be appreciated that imaging element 11 may be fixedly secured within applier 10. Of course, as with other components described above, the foregoing components are optional, and a variety of other configurations may be used to facilitate viewing of images captured by imaging element 11, as well as alternate configurations for coupling imaging element 11 or other parts of applier 10 to other devices.

In use, applier 10 may be inserted adjacent an anastomotic opening in proximate tissue walls 46, 48. Tip 13 may be located in the retracted position, allowing imaging element 11 to capture a forward view through clear tip point 17. Once tip 13 is inserted through the anastomotic opening, tip 13 may be extended using tip actuator 18. With tip 13 in the extended position, imaging element 11 may capture a retrograde view reflected off mirrored proximal edge 20 of tip 13. Sheath actuator 28 may be used to retract sheath 24 to expose ring deployment mechanism 26. After an anastomotic ring 14 has been deployed, tip 13 may be withdrawn through the anastomotic opening and tip 13 may be moved to the retracted position using tip actuator 18 so that the anastomotic attachment may be viewed from the front to confirm proper deployment. Other variations of use of applier 10 will be apparent to those of ordinary skill in the art.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings. Additional advantages may readily appear to those skilled in the art.

What is claimed is:

1. A surgical instrument for implanting an anastomotic ring device at an anastomosis site, comprising:

(i) a handle;

(ii) a closed elongate shaft comprising a proximal portion and a distal portion, the proximal portion being connected to the handle, wherein the elongate shaft further comprises a tip on the distal portion of the elongate shaft, wherein the tip comprises a mirrored proximal portion, wherein the tip is moveable from a retracted position to an extended position, wherein the tip distally terminates into a tip point, wherein the tip comprises an interior cavity between the mirrored proximal portion and the tip point;

(iii) a ring deployment mechanism on the distal portion of the shaft, the ring deployment mechanism being configured to receive and deploy an anastomotic ring, wherein the ring deployment mechanism is configured to receive and deploy the anastomotic ring independently from movement of the tip between a retracted position and an extended position; and (iv) one or more imaging elements positioned on or in the elongate shaft, wherein at least one of the one or more imaging elements is operable to capture a forward image when the tip is in the retracted position, and wherein at least one of the one or more imaging elements is operable to capture a retrograde image from the mirrored proximal portion of the tip when the tip is in the extended position, wherein at least one of the one or more imaging elements extends distally beyond the mirrored proximal portion of the tip into the interior cavity of the tip when the tip is in the retracted position.

2. The surgical instrument of claim 1, wherein at least one of the one or more imaging elements comprises one or more imaging fibers.

3. The surgical instrument of claim 1, further comprising one or more illumination fibers operatively configured to transmit light to the distal portion of the elongate shaft to aid the imaging element in capturing an image.

4. The surgical instrument of claim 1, wherein the tip comprises a substantially optically clear tip point.

5. The surgical instrument of claim 4, further comprising a tip actuator operable to move the tip between the retracted position and the extended position.

6. The surgical instrument of claim 5, further comprising a guide tube connected to the tip actuator.

7. The surgical instrument of claim 6, further comprising a plurality of connectors connecting the guide tube to the tip.

8. The surgical instrument of claim 1, further comprising a clamp mechanism configured to couple at least one of the one or more imaging elements to an image amplification device.

9. The surgical instrument of claim 8, wherein the shaft further comprises a retractable sheath.

10. The surgical instrument of claim 1, wherein:
(i) the ring deployment mechanism comprises a proximal portion and a distal portion; and
(ii) at least one of the one or more imaging members is operable to capture a retrograde image from the mirrored proximal portion of the tip when at least one of the proximal portion or the distal portion of the ring deployment mechanism is in an actuated position.

11. A surgical instrument for implanting an anastomotic ring device at an anastomosis site, comprising:
(i) a handle;
(ii) an elongate shaft comprising a proximal portion and a distal portion, the proximal portion being connected to the handle, wherein the elongate shaft distally terminates into a closed tip, wherein the tip comprises a mirrored proximal portion, wherein the tip is moveable from a retracted position to an extended position, wherein the mirrored proximal portion comprises a channel centrally located within the mirrored proximal portion;

(iii) a ring deployment mechanism on the distal portion of the shaft, the ring deployment mechanism being configured to receive and deploy an anastomotic ring, wherein the ring deployment mechanism comprises a proximal portion and distal portion;

(iv) one or more imaging elements positioned on the distal portion of the elongate shaft, the one or more imaging elements being operatively configured to capture an image of a forward view and a retrograde view of the anastomosis site, wherein at least one of the one or more imaging elements is operable to capture an image of a retrograde view of the anastomosis site when at least one of the proximal portion or the distal portion of the ring deployment mechanism is in an actuated position, the one or more imaging elements terminating in a distal end, wherein at least one of the one or more imaging elements passes through the channel in the mirrored proximal portion into the tip when the tip is in the retracted position, wherein the at least one of the one or more imaging elements is configured to capture a forward view of the anastomosis site through the tip, wherein the distal end of the at least one or more imaging elements is positioned proximal of the mirrored proximal portion when the tip is in the extended position.

12. The surgical instrument of claim 11, wherein:
(i) the elongate shaft further comprises a tip on the distal portion of the elongate shaft, wherein the tip comprises a mirrored proximal portion, wherein the tip is moveable from a retracted position to an extended position;
(ii) the ring deployment mechanism is configured to receive and deploy the anastomotic ring independently of movement of the tip between a retracted position and an extended position; and
(iii) at least one of the one or more imaging members is operable to capture an image of a retrograde view of the anastomosis site from the mirrored proximal portion of the tip when the tip is in the extended position.

13. A surgical instrument for implanting an anastomotic ring device at an anastomosis site, comprising:
(i) an actuating member configured to receive an anastomotic ring and moveable between a cylindrical, unactuated position and a hollow rivet forming position in response to a compressive actuating force;
(ii) a handle including an actuation mechanism operable to produce the compressive actuating force;
(iii) an elongate shaft connecting the handle to the actuating member and operatively configured to transfer the compressive actuating force from the handle to the actuating member, wherein the elongate shaft comprises a tip on a distal portion of the elongate shaft, wherein the tip comprises a mirrored proximal portion, wherein the tip is moveable from a retracted position to an extended position, wherein the tip distally terminates into a tip point, wherein the tip further comprises an interior cavity between the mirrored proximal portion and the tip point; and
(iv) one or more imaging elements positioned on or in the elongate shaft, wherein the one or more imaging elements are operable to capture a view of an anastomosis site, wherein at least one of the one or more imaging elements extends distally beyond the mirrored proximal portion of the tip into the interior cavity of the tip when the tip is in the retracted position.

14. The surgical instrument of claim 13, further comprising a pair of input members configured to receive user input to generate the compressive actuating force.

15. The surgical instrument of claim 14, further comprising a locking element configured to prevent inadvertent engagement of the input members.

16. The surgical instrument of claim 15, wherein the input members are each slideable from a first, unactuated position to a second, actuated position.

17. The surgical instrument of claim 16, wherein the locking element is moveable from a locked position to an unlocked position, wherein the locking element is configured to prevent the input members from sliding to the second, actuated position when in the locking element is in the locked position.

18. The surgical instrument of claim 13, wherein:
(i) the actuating member is configured to move between a cylindrical, unactuated position and a hollow rivet forming position in response to a compressive actuating force independently of movement of the tip between a retracted position and an extended position; and
(ii) at least one of the one or more imaging members is operable to capture a retrograde view of the anastomosis site from the mirrored proximal portion of the tip when the tip is in the extended position.

19. The surgical instrument of claim 13, wherein:
(i) the actuating member comprises a proximal portion and a distal portion; and
(ii) at least one of the one or more imaging members is operable to capture a retrograde view of the anastomosis site when at least one of the proximal portion or the distal portion of the actuating member is in an actuated position.

20. The surgical instrument of claim 13, wherein:
(i) the actuating member comprises a proximal portion and a distal portion;
(ii) the actuating member is configured to move between a cylindrical, unactuated position and a hollow rivet forming position in response to a compressive actuating force independently of movement of the tip between a retracted position and an extended position; and
(iii) at least one of the one or more imaging members is operable to capture a retrograde view of the anastomosis site from the mirrored proximal portion of the tip when the tip is in the extended position and when at least one of the proximal portion or the distal portion of the actuating member is in an actuated position.

* * * * *